US008153395B2

(12) United States Patent
Nørgaard

(10) Patent No.: US 8,153,395 B2
(45) Date of Patent: Apr. 10, 2012

(54) METHOD OF MAKING ACTIVATED CARBOXYPEPTIDASES

(75) Inventor: Per Nørgaard, Humlebæk (DK)

(73) Assignee: Novo Nordisk A/S, Bagsvaerd (DK)

( * ) Notice: Subject to any disclaimer, the term of this patent is extended or adjusted under 35 U.S.C. 154(b) by 79 days.

(21) Appl. No.: 12/312,663

(22) PCT Filed: Nov. 21, 2007

(86) PCT No.: PCT/EP2007/062629
§ 371 (c)(1),
(2), (4) Date: Sep. 2, 2009

(87) PCT Pub. No.: WO2008/062010
PCT Pub. Date: May 29, 2008

(65) Prior Publication Data
US 2010/0173357 A1 Jul. 8, 2010

Related U.S. Application Data

(60) Provisional application No. 60/861,155, filed on Nov. 27, 2006.

(30) Foreign Application Priority Data

Nov. 22, 2006 (EP) .................................... 06124576

(51) Int. Cl.
*C12P 21/06* (2006.01)
(52) U.S. Cl. ...................................................... 435/68.1
(58) Field of Classification Search .................. None
See application file for complete search history.

(56) References Cited

U.S. PATENT DOCUMENTS

| 4,914,026 A | 4/1990 | Brake et al. |
| 6,337,194 B1 | 1/2002 | Hadfield et al. |
| 6,348,327 B1 | 2/2002 | Gorman et al. |

FOREIGN PATENT DOCUMENTS

| EP | 163529 | 12/1985 |
| WO | WO9535384 | 12/1985 |
| WO | WO 90/10075 | 9/1990 |
| WO | WO95/02059 | 1/1995 |
| WO | WO 97/03089 | 1/1997 |
| WO | WO 2007/020256 | 2/2007 |
| WO | WO 2008/037735 | 4/2008 |

OTHER PUBLICATIONS

Graham, T. R. et al., "Compartmental Organization of Gogi-specific Protein Modification and Vacuolar Protein Sorting Events Defined in a Yeast sec18 (NSF) Mutant", Journal of Cell Biology, 1991, vol. 114, No. 2, pp. 207-218.
Hopkins, B.D. et al., "Introduction of Kex2 Cleavage Sites in Fusion Proteins for Monitoring Localization and Transport in Yeast Secretory Pathway", Methods in Enzymology, vol. 327, 2000, pp. 107-118.
Kjeldsen, T., "Yeast Secretory Expression of Insulin Precursors", Appl. Microbiol. Biotechnol., 2000, vol. 54, No. 3, pp. 277-286.
Rockwell, N.C. et al., "Interplay Between $S_1$ and $S_4$ Su bsites in Kex2 Protease: Kex2 Exhibits Dual Specificity for the $P_4$Side Chain", Biochemistry, 1998, vol. 37, No. 10, pp. 3386-3391.
Thim, L. et al., "Secretion of Human Insulin by a Transformed Yeast Cell", FEBS Letters, 1987, vol. 212, No. 2, pp. 307-312.
Bevan, Alison et al, Quantitative Assessment of Enzyme Specificity In Vivo: P2 Recognition by Kex2 Protease Defined in a Genetic System, Proceedings of the National Academy of Sciences of the USA vol. 95(18), pp. 10384-10389 (1998).
Frank, Pettee, Zimmerman and Burck, The Production of Human Proinsulin and its Transformation to Human Insulin and C-Peptides, Ricii, Gross, Pierce Ciiemical Company. Rockford Illinois, p. 729 (1981).
Hunt, S M N et al, Processing of Mutated Human Proinsulin to Mature Insulin in the Non-Endocrine Cell Line, Cho, Cytotechnology, vol. 21, pp. 279-288 (1996).
Thim et al, Secretion and Processing of Insulin Precursors in Yeast, Proceedings of the National Academy of Sciences of the United States, vol. 83, pp. 6766-6770 (1986).

*Primary Examiner* — Gary B. Nickol
*Assistant Examiner* — Khatol Shahnan-Shah
(74) *Attorney, Agent, or Firm* — Michael J. Brignati

(57) ABSTRACT

The invention is related to a method for making an activated carboxypeptidase in a fungi cell comprising introducing a DNA sequence encoding a proform of the carboxypeptidase wherein a Kex2 site has been introduced in the prosequence of the carboxypeptidase, culturing the fungi cell under conditions suitable for expression of the procarboxypeptidase and cleaving off the prosequence within the cell to liberate the free active form of the carboxypeptidase. The invention is also related to methods for making mature human insulin and human insulin analogues by use of the activated carboxypeptidase enzyme.

8 Claims, 4 Drawing Sheets

(4 of 4 Drawing Sheet(s) Filed in Color)

SEQUENCE LISTING

```
<160> NUMBER OF SEQ ID NOS: 9

<210> SEQ ID NO 1
<211> LENGTH: 40
<212> TYPE: PRT
<213> ORGANISM: Saccharomyces cerevisiae

<400> SEQUENCE: 1

Lys Pro Lys Phe Pro Glu Ala Ile Lys Thr Lys Lys Asp Trp Asp Phe
1               5                   10                  15

Val Val Lys Asn Asp Ala Ile Glu Asn Tyr Gln Leu Arg Val Asn Lys
            20                  25                  30

Ile Lys Asp Pro Lys Ile Leu Gly
        35                  40
```

<210> SEQ ID NO 2
<211> LENGTH: 41
<212> TYPE: PRT
<213> ORGANISM: Saccharomyces cerevisiae

<400> SEQUENCE: 2

Lys Pro Lys Phe Pro Glu Ala Ile Lys Thr Lys Lys Asp Trp Asp Phe
1               5                   10                  15

Val Val Lys Asn Asp Ala Ile Glu Asn Tyr Gln Leu Arg Val Asn Lys
            20                  25                  30

Ile Lys Arg Asp Pro Lys Ile Leu Gly
        35                  40

<210> SEQ ID NO 3
<211> LENGTH: 40
<212> TYPE: PRT
<213> ORGANISM: Saccharomyces cerevisiae

<400> SEQUENCE: 3

Lys Pro Lys Phe Pro Glu Ala Ile Lys Thr Lys Lys Asp Trp Asp Phe
1               5                   10                  15

Val Val Lys Asn Asp Ala Ile Glu Asn Tyr Gln Leu Arg Val Leu Gly
            20                  25                  30

Lys Arg Asp Pro Lys Ile Leu Gly
        35                  40

<210> SEQ ID NO 4
<211> LENGTH: 42
<212> TYPE: PRT
<213> ORGANISM: Saccharomyces cerevisiae

<400> SEQUENCE: 4

Leu Gly Lys Arg Glu Phe Pro Glu Ala Ile Lys Thr Lys Lys Asp Trp
1               5                   10                  15

Asp Phe Val Val Lys Asn Asp Ala Ile Glu Asn Tyr Gln Leu Arg Val
            20                  25                  30

Asn Lys Ile Lys Asp Pro Lys Ile Leu Gly
        35                  40

<210> SEQ ID NO 5
<211> LENGTH: 40
<212> TYPE: PRT
<213> ORGANISM: Saccharomyces cerevisiae

<400> SEQUENCE: 5

Lys Pro Lys Phe Pro Glu Ala Ile Lys Thr Lys Arg Asp Trp Asp Phe
1               5                   10                  15

Val Val Lys Asn Asp Ala Ile Glu Asn Tyr Gln Leu Arg Val Asn Lys
            20                  25                  30

Ile Lys Asp Pro Lys Ile Leu Gly
        35                  40

<210> SEQ ID NO 6
<211> LENGTH: 40
<212> TYPE: PRT
<213> ORGANISM: Saccharomyces cerevisiae

<400> SEQUENCE: 6

Lys Pro Lys Phe Pro Glu Ala Ile Lys Thr Lys Lys Asp Trp Asp Phe
1               5                   10                  15

```
Val Lys Arg Asn Asp Ala Ile Glu Asn Tyr Gln Leu Arg Val Asn Lys
            20                  25                  30

Ile Lys Asp Pro Lys Ile Leu Gly
        35                  40

<210> SEQ ID NO 7
<211> LENGTH: 42
<212> TYPE: PRT
<213> ORGANISM: Saccharomyces cerevisiae

<400> SEQUENCE: 7

Lys Pro Lys Phe Pro Glu Ala Ile Lys Thr Lys Lys Asp Trp Asp Phe
1               5                   10                  15

Val Val Lys Leu Asp Lys Arg Ala Ile Glu Asn Tyr Gln Leu Arg Val
            20                  25                  30

Asn Lys Ile Lys Asp Pro Lys Ile Leu Gly
        35                  40

<210> SEQ ID NO 8
<211> LENGTH: 43
<212> TYPE: PRT
<213> ORGANISM: Saccharomyces cerevisiae

<400> SEQUENCE: 8

Lys Pro Lys Phe Pro Glu Ala Ile Lys Thr Lys Lys Asp Trp Asp Phe
1               5                   10                  15

Val Val Lys Asn Asp Ala Ile Glu Asn Tyr Gln Leu Arg Val Asn Lys
            20                  25                  30

Ile Lys Asp Pro Lys Arg Gly Gly Ile Leu Gly
        35                  40

<210> SEQ ID NO 9
<211> LENGTH: 9
<212> TYPE: PRT
<213> ORGANISM: Artificial
<220> FEATURE:
<223> OTHER INFORMATION: C-peptide

<400> SEQUENCE: 9

Leu Ala Arg Arg Asp Leu Gly Lys Arg
1               5
```

METHOD OF MAKING ACTIVATED CARBOXYPEPTIDASES

CROSS-REFERENCE TO RELATED APPLICATIONS

This application is a 35 U.S.C. §371 national stage application of International Patent Application PCT/EP2007/062629 (published as WO 2008/062010 A3), filed Nov. 21, 2007, which claimed priority of European Patent Application 06124576.7, filed Nov. 22, 2006; this application further claims priority under 35 U.S.C. §119 of U.S. Provisional Application 60/861,155, filed Nov. 27, 2006.

FIELD OF THE INVENTION

The present invention is related to a method for making activated carboxypeptidases and a method for use of the activated carboxypeptidases for the production of mature human insulin or human insulin analogues in fungi cells.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Nov. 20, 2007. The Sequence Listing is made up of 4 KB, and the information contained in the attached "SEQUENCE LISTING" is identical to the information in the specification as originally filed. No new matter is added.

BACKGROUND OF THE INVENTION

Insulin is a polypeptide hormone produced in the beta cells of the islets of Langerhans. The active insulin molecule is a two-chain molecule consisting of a B- and an A-chain connected by two disulphide bridges. The insulin is synthesized as a precursor molecule proinsulin with the structure B-C-A wherein the C-peptide chain connects the C-terminal amino acid residue in the B-chain with the N-terminal amino acid residue in the A-chain. Mature two-chain insulin is formed by in vivo cleavage of the C-peptide at the pair of basic amino acid residues situated at the junction with the A- and B-chain. The A- and B-chain are held together by two disulphide bridges between the A7 and B7 and the A20 and B19 Cys residues, respectively. In addition, the biologically active insulin molecule has an internal disulphide bridge between the Cys residues in the position A6 and A11.

After the development of recombinant DNA technology numerous methods have been described to produce insulin and precursors thereof in genetically modified host cells. As *E. coli* does not have the cellular machinery for folding the expressed polypeptide and establish the disulphide bridges connecting the A- and B chain in the mature insulin this strategy includes a number of in vitro processing steps such as in vitro establishment of the disulphide bridges during refolding and subsequent cleavage of the C-peptide.

In contrast to *E. coli* eukaryotes contain the necessary machinery for folding and establishing disulphide bridges and thus would seem to be good candidates for production of mature insulin in genetically modified organisms. Thim et al, in FEBS Letters, volume 212, number 2, 307-312 disclose expression of human proinsulin and a number of insulin precursors with certain modified C-peptides. U.S. Pat. No. 4,914,026 discloses a process for making mature insulin in yeast by insertion of the human proinsulin gene linked to the yeast a-factor leader sequence in a yeast host cell and growing the transformed yeast cell in a nutrient medium under conditions whereby proinsulin is expressed and secreted in mature form.

WO 97/03089 disclose expression of insulin precursors with the formula BZA wherein B and A are the A and B peptide chains of human insulin being linked by at least one disulphide bond and Z is a polypeptide comprising at least one proteolytic cleavage site. WO 90/10075 disclose processes for making insulin and insulin analogues based on expression of a precursor of the insulin or insulin analogue in yeast that following initial recovery from the fermentation broth are enzymatically converted to the mature insulin or insulin analogue. The precursor molecules comprise certain modified C-peptides and may furthermore comprise an N-terminal extension of the insulin B-chain. The modified C-peptide and the possible N-terminal extension of the B-peptide are designed not to be cleaved in the yeast cell and thus the precursors are secreted as single chain peptides wherein the A- and the B-chain are still connected by the modified C-peptide but with correctly positioned disulphide bridges. The mature insulin or insulin analogue product is then obtained by a number of subsequent in vitro enzymatic steps to cleave the C-peptide and possibly the N-terminal extension. These enzymatic steps are time consuming, often costly and introduce additional impurities that subsequently have to be removed in further downstream process steps like expensive chromatography steps and the like.

A process for making mature insulin in genetically engineered animal cells that are not naturally capable of forming secretory granules is disclosed in U.S. Pat. No. 6,348,327.

The purpose of the present invention is to develop a fungi strain capable of producing carboxypeptidases that are intracellularly activated independently of proteinase A and B and furthermore to develop a process to make fully processed mature insulin or insulin analogues by means of such an alternatively activated carboxypeptidase so that expensive and time consuming downstream purification process steps are avoided.

SUMMARY OF THE INVENTION

In one aspect the present invention is related to a method for making an activated carboxypeptidase comprising expressing in a fungi cell a DNA sequence encoding a modified proform of the carboxypeptidase comprising an inserted Kex2 cleavage site whereupon the proform of the carboxypeptidase is cleaved within the cell to liberate the free, active form of the carboxypeptidase.

In one embodiment of the invention the method further comprises a step of isolating the active form of the carboxypeptidase from the fungi cell.

In a further embodiment of the invention the fungi cell has a non functional PEP4 gene (the gene encoding proteinase A).

In one embodiment of the invention the fungi cell has a deleted PEP4 gene.

The Kex2 site inserted in the proform of the carboxypeptidase in a position ensuring efficient cleavage of the proform of the carboxypeptidase to form the activated mature form of the carboxypeptidase.

In one embodiment of the present invention the Kex2 site is attached directly to the natural N-terminal amino acid residue in the wildtype carboxypeptidase.

In another embodiment the Kex2 site is introduced in a position in relatively close proximity to the natural N-terminal amino acid residue of the caboxypeptidase. However, the Kex2 site should preferably not be more than about 30 amino acid residues upstream or downstream to the natural N-terminal amino acid residue of the caboxypeptidase.

In one embodiment of the invention the Kex2 site is introduced in a distance of from 1 to about 30 amino acid residues upstream or downstream to the natural N-terminal amino acid residue in the carboxypeptidase.

In one embodiment of the invention the Kex2 site is introduced in a distance of from 1 to about 30 amino acid residues upstream to the natural N-terminal amino acid residue in the carboxypeptidase.

In a further embodiment of the invention the Kex2 cleavage site is introduced in a distance of from 2-30 amino acid residues upstream to the natural N-terminal amino acid residue in f the carboxypeptidase.

In a further embodiment of the invention the Kex2 cleavage site is introduced in a distance of from 5-30 amino acid residues upstream to the natural N-terminal amino acid residue in the carboxypeptidase.

In a further embodiment of the invention the Kex2 cleavage site is introduced in a distance of from 5-20 amino acid residues upstream to the natural N-terminal amino acid residue in the carboxypeptidase In another embodiment the Kex2 site is introduced in a distance of from 2-30, from 2-29, from 2-28, from 2-27, from 2-26, from 2-25, from 2-24, from 2-23, from 2-22, from 2-21 or from 2-20, amino acid residues upstream or downstream of the natural N-terminal acid residue of the carboxypeptidase.

In a further embodiment the Kex2 site is introduced in a distance of from 3-30, from 3-29, from 3-28, from 3-27, from 3-26, from 3-25, from 3-24, from 3-23, from 3-22, from 3-21 or from 3-20 amino acid residues upstream or downstream of the natural N-terminal acid residue of the carboxypeptidase.

In a further embodiment the Kex2 site is introduced in a distance of from 4-30, from 4-29, from 4-28, from 4-27, from 4-26, from 4-25, from 4-24, from 4-23, from 4-22, from 4-21 or from 4-20 amino acid residues upstream or downstream of the natural N-terminal acid residue of the carboxypeptidase.

In a further embodiment the Kex2 site is introduced in a distance of from 5-30, from 5-29, from 5-28, from 5-27, from 5-26, from 5-25, from 5-24, from 5-23, from 5-22, from 5-21 or from 5-20 amino acid residues upstream or downstream of the natural N-terminal acid residue of the carboxypeptidase.

In a further embodiment the Kex2 site is introduced in a distance of 1 amino acid residue upstream or downstream of the natural N-terminal acid residue of the carboxypeptidase.

In a further embodiment the Kex2 site is introduced in a distance of 2 amino acid residues upstream or downstream of the natural N-terminal acid residue of the carboxypeptidase.

In a further embodiment the Kex2 site is introduced in a distance of 3 amino acid residues upstream or downstream of the natural N-terminal acid residue of the carboxypeptidase.

In a further embodiment the Kex2 site is introduced in a distance of 4 amino acid residues upstream or downstream of the natural N-terminal acid residue of the carboxypeptidase.

In a further embodiment the Kex2 site is introduced in a distance of 5 amino acid residues upstream or downstream of the natural N-terminal acid residue of the carboxypeptidase.

In a further embodiment the Kex2 site is introduced in a distance of 6 amino acid residues upstream or downstream of the natural N-terminal acid residue of the carboxypeptidase.

In a further embodiment the Kex2 site is introduced in a distance of 7 amino acid residues upstream or downstream of natural N-terminal acid residue of the carboxypeptidase.

In a further embodiment the Kex2 site is introduced in a distance of 8 amino acid residues upstream or downstream of the natural N-terminal acid residue of the carboxypeptidase.

In a further embodiment the Kex2 site is introduced in a distance of 9 amino acid residues upstream or downstream of the natural N-terminal acid residue of the carboxypeptidase.

In a further embodiment the Kex2 site is introduced in a distance of 10 amino acid residues upstream or downstream of the natural N-terminal acid residue of the carboxypeptidase.

In a further embodiment the Kex2 site is introduced in a distance of 12 amino acid residues upstream or downstream of the natural N-terminal acid residue of the carboxypeptidase.

In a further embodiment the Kex2 site is introduced in a distance of 13 amino acid residues upstream or downstream of the natural N-terminal acid residue of the carboxypeptidase.

In a further embodiment the Kex2 site is introduced in a distance of 14 amino acid residues upstream or downstream of the natural N-terminal acid residue of the carboxypeptidase.

In a further embodiment the Kex2 site is introduced in a distance of 15 amino acid residues upstream or downstream of the natural N-terminal acid residue of the carboxypeptidase.

In a further embodiment the Kex2 site is introduced in a distance of 16 amino acid residues upstream or downstream of the natural N-terminal acid residue of the carboxypeptidase.

In a further embodiment the Kex2 site is introduced in a distance of 17 amino acid residues upstream or downstream of the natural N-terminal acid residue of the carboxypeptidase.

In a further embodiment the Kex2 site is introduced in a distance of 18 amino acid residues upstream or downstream of the natural N-terminal acid residue of the carboxypeptidase.

In a further embodiment the Kex2 site is introduced in a distance of 19 amino acid residues upstream or downstream of the natural N-terminal acid residue of the carboxypeptidase.

In a further embodiment the Kex2 site is introduced in a distance of 20 amino acid residues upstream or downstream of the natural N-terminal acid residue of the carboxypeptidase.

In a further embodiment the Kex2 site is introduced in a distance of 21 amino acid residues upstream or downstream of the natural N-terminal acid residue of the carboxypeptidase.

In a further embodiment the Kex2 site is introduced in a distance of 22 amino acid residues upstream or downstream of the natural N-terminal acid residue of the carboxypeptidase.

In a further embodiment the Kex2 site is introduced in a distance of 23 amino acid residues upstream or downstream of the natural N-terminal acid residue of the carboxypeptidase.

In a further embodiment the Kex2 site is introduced in a distance of 24 amino acid residues upstream or downstream of the natural N-terminal acid residue of the carboxypeptidase.

In a further embodiment the Kex2 site is introduced in a distance of 25 amino acid residues upstream or downstream of the natural N-terminal acid residue of the carboxypeptidase.

In a further embodiment the Kex2 site is introduced in a distance of 26 amino acid residues upstream or downstream of the natural N-terminal acid residue of the carboxypeptidase.

In a further embodiment the Kex2 site is introduced in a distance of 27 amino acid residues upstream or downstream of the natural N-terminal acid residue of the carboxypeptidase.

In a further embodiment the Kex2 site is introduced in a distance of 28 amino acid residues upstream or downstream of the natural N-terminal acid residue of the carboxypeptidase.

In a further embodiment the Kex2 site is introduced in a distance of 29 amino acid residues upstream or downstream of the natural N-terminal acid residue of the carboxypeptidase.

In a further embodiment the Kex2 site is introduced in a distance of 30 amino acid residues upstream or downstream of the natural N-terminal acid residue of the carboxypeptidase.

In a further aspect the invention is related to a method for making mature human insulin or an analogue thereof by reacting a precursor for human insulin or an analogue thereof comprising a C-terminal extension of the B-chain with a carboxypeptidase produced by a method according to any of the above embodiments, whereby the C-terminal extension is cleaved off to give mature human insulin or an analogue thereof.

In one aspect the invention is related to a method for making mature human insulin or an analogue thereof comprising coexpressing in a fungi cell
i) a DNA sequence encoding a precursor of human insulin or an analogue thereof comprising a C-terminal extension of the B-chain and
ii) a DNA sequence encoding a proform of a carboxypeptidase comprising a Kex2 cleavage site
whereby the C-terminal extension of the B-chain in the insulin precursor molecule is cleaved off by the co-expressed and activated carboxypeptidase within the fungal cell, whereupon the mature human insulin or an analogue thereof is isolated from the culture medium.

The carboxypeptidase may be any suitable carboxypeptidase. However, in one embodiment of the invention the carboxypeptidase is endogen to the host fungi cell. In a further embodiment the carboxypeptidase is CPY.

In one embodiment the method the precursor of human insulin or an analogue thereof comprises the B-chain of human insulin or an analogue thereof, the A-chain of human insulin or an analogue thereof and a C-peptide linking the B-chain and the A-chain together, wherein the C-peptide comprises at least one Kex2 cleavage site and wherein the B-chain comprises a C-terminal extension facilitating a more efficient Kex2 cleavage of the C-peptide within the fungi cell and is further capable of being cleaved off with a carboxypeptidase.

The amino acid sequence attached to the C-terminal amino acid residue of the B-chain will be relatively short and will typically have from 1-4 or 1-3 amino acid residues or in particular 2 amino acid residues. The amino acid residues in this sequence will be hydrophobic amino acid residues and will typically be selected from the group consisting of Phe, Leu, Ile, Tyr, Trp, Val, Met and Ala.

Non limiting examples of C-terminal extension to the B-chain are Leu-Gly; Leu-Ala; Leu-Leu; Leu-Met and Leu-Ile.

In one embodiment of the invention the C-peptide in the insulin precursor will comprise a single Kex2 site attached directly to the N-terminal amino acid residue in the A-chain to ensure cleavage at this position.

In a further embodiment of the invention the C-peptide will comprise two Kex2 cleavage sites with a peptide sequence interposed between the two Kex2 sites. The length and the amino acid composition of the peptide sequence between the two Kex2 sites may vary as long as it enables folding of the expressed single-chain insulin precursor and establishing of the correct positioned disulfide bridges in the insulin precursor molecule.

The size of the natural C-peptide is of 35 amino acid residues. Thus in one aspect of the present invention the peptide sequence between the two Kex2 sites will be of about the same length as the natural C-peptide.

In one embodiment the peptide sequence between the two Kex2 sites will be 1-35, 1-34, 1-33, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3 or 1-2 amino acid residues long.

In one embodiment of the invention the human insulin precursor has the amino acid sequence

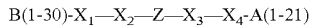

B(1-30)-$X_1$—$X_2$—Z—$X_3$—$X_4$-A(1-21)

where B(1-30) is the B-chain of human insulin or an analogue thereof, A(1-21) is the human insulin A chain or an analogue thereof, $X_1$ is a peptide sequence of 1-5 amino acid residues which will facilitate a more efficient Kex2 cleavage within the fungi cell, $X_2$ is a Kex2 cleavage site, Z is a peptide sequence with from 1 to about 35 amino acid residues or a peptide bond, $X_3$ is a Kex2 cleavage site or a peptide bond and $X_4$ is an aminopeptidase cleavage site or a peptide bond.

In one embodiment of the invention $X_3$ is a Kex2 cleavage site, Z is a peptide sequence and $X_4$ is peptide bond.

In another embodiment of the invention $X_3$ and Z are peptide bonds and $X_4$ is an aminopeptidase cleavage site.

$X_1$ is typically from 1-4 or from 1-3 amino acid residues long and in one embodiment $X_1$ is a peptide sequence of 2 amino acid residues. The amino acid residues in $X_1$ will be preferably be hydrophobic amino acid residues and will typically be selected from the group consisting of Phe, Leu, Ile, Tyr, Trp, Val, Met and Ala.

In another embodiment the amino acid residues in $X_1$ is selected from the group consisting of Phe, Leu, Ile, Tyr, Trp, Val, Met, Ala, Asp and Gly.

In one embodiment of the invention $X_1$ is Leu-Ala.
In another embodiment of the invention $X_1$ is Phe-Leu.
In another embodiment of the invention $X_1$ is Leu-Gly.
In another embodiment of the invention $X_1$ is Leu-Leu.
In another embodiment of the invention $X_1$ is Leu-Met.
In another embodiment of the invention $X_1$ is Leu-Ile.

BRIEF DESCRIPTION OF THE DRAWINGS

The patent or application file contains at least one drawing executed in color. Copies of this patent or patent application publication with color drawing(s) will be provided by the Office upon request and payment of necessary fee.

DETAILED DESCRIPTION OF THE INVENTION

Figure 1:
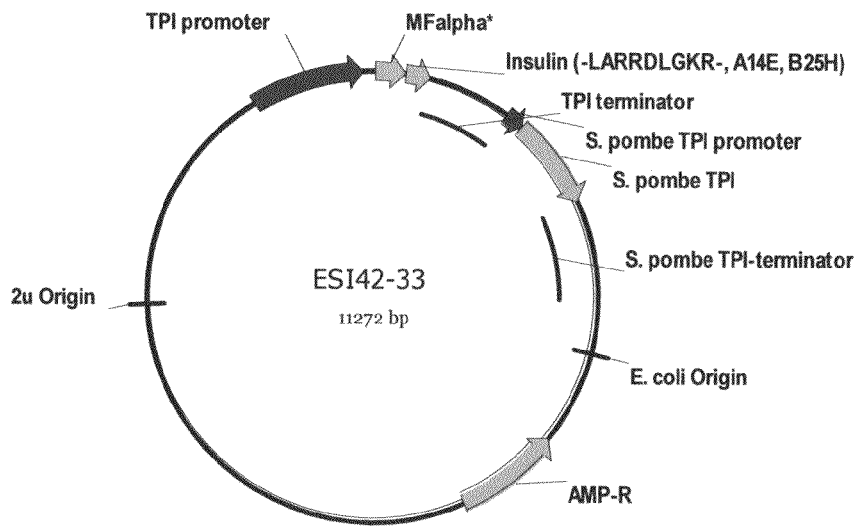
FIG. 1 shows plasmid ESI42-33.

Carboxypeptidase Y (CPY) is in the yeast Saccharomyces cerevisiae synthesized as an inactive pro-form (proCPY).

After translocation of the protein into the Endoplasmic Reticulum (ER), it is transported to the vacuole. Upon arrival, it is activated by removal of the propeptide, a proteolytic event initiated by proteinase A. Two scenarios prevent efficient conversion of proCPY to CPY: 1) If the PEP4 gene (the gene encoding proteinase A) is deleted or inactivated, all CPY will be on the inactive pro-form. 2) If PRC1 (the gene encoding CPY) is overexpressed, a significant amount of proCPY will be secreted to the fermentation broth. This will remain in the pro-form since proteinase A is located to the vacuole and thereby separated from the secreted proCPY. In order to allow efficient activation of proCPY in these situations, an alternative activation pathway is required.

In the interface between the pro-peptide and the mature CPY are located sequence motifs that can be recognized by proteinase A, thereby leading to specific cleavage. Upon cleavage, the pro-peptide separates from the mature CPY. In the present invention, a number of mutants have been made, in which residues close to the interface between the pro-peptide and the mature CPY have been mutated in such a way that a dibasic cleavage site recognized by Kex2p has been inserted. This ensures conversion of proCPY to CPY in the Golgi apparatus, where Kex2p is localized. This removes the need for proteinase A in the activation of CPY. Furthermore, the mutated genes have been overexpressed, in order to allow secretion of significant amounts of active CPY.

In the following are shown the amino acid sequence of the prosequence of the wildtype CPY carboxypeptidase from position 31 upstream of the natural N-terminal amino acid residue of the wild type enzyme and the first 9 amino acid residue from the N-terminal end of the wild type enzyme and corresponding sequences from mutants A-G wherein a Kex2 site (KR) has been inserted at different positions upstream or downstream in relation to the N-terminal amino acid residue. The cleavage place for cleaving off the prosequence is indicated with an arrow.

```
Wildtype:
                                         (SEQ ID NO: 1)
KPKFPEAIKTKKDWDFVVKNDAIENYQLRVN↓KIKDPKILG.

Mutant A:
                                         (SEQ ID NO: 2)
KPKFPEAIKTKKDWDFVVKNDAIENYQLRVNKIKR↓DPKILG.

Mutant B:
                                         (SEQ ID NO: 3)
KPKFPEAIKTKKDWDFVVKNDAIENYQLRVLGKR↓DPKILG.

Mutant C:
                                         (SEQ ID NO: 4)
LGKR↓EFPEAIKTKKDWDFVVKNDAIENYQLRVNKIKDPKILG.

Mutant D:
                                         (SEQ ID NO: 5)
KPKFPEAIKTKR↓DWDFVVKNDAIENYQLRVNKIKDPKILG.

Mutant E:
                                         (SEQ ID NO: 6)
KPKFPEAIKTKKDWDFVKR↓NDAIENYQLRVNKIKDPKILG.

Mutant F:
                                         (SEQ ID NO: 7)
KPKFPEAIKTKKDWDFVVKLDKR↓AIENYQLRVNKIKDPKILG.

Mutant G:
                                         (SEQ ID NO: 8)
KPKFPEAIKTKKDWDFVVKNDAIENYQLRVNKIKDPKR↓GILG.
```

The term "pro-peptide" or "prosequence" as used herein means a polypeptide sequence whose function is to facilitate the folding and transport of the expressed polypeptide from the endoplasmic reticulum to its final destination within the secretory pathway or extracellularly. The pro-peptide furthermore inhibits the enzymatic activity of the carboxypeptidase.

The term "proform" means the fusion product of the prosequence and the active polypeptide sequence.

The carboxypeptidase may be any carboxypeptidase which can be expressed in a fungi cell and which can be activated by an endogenous Kex2p enzyme expressed by the fungi cell.

Representative examples of carboxypeptidases are carboxypeptidase A (EC 3.4.17.1), carboxypeptidase A2 (EC 3.4.17.15), carboxypeptidase B (EC 3.4.17.2), carboxypeptidase E (EC 3.4.17.10), carboxypeptidase M (EC 3.4.17.12), carboxypeptidase T (EC 3.4.17.18), carboxypeptidase U (EC 3.4.17.20) and carboxypeptidase Y (EC 3.4.16.5), In one embodiment of the invention the carboxypeptidase is CPY.

If the introduced Kex2 site is attached directly to the N-terminal amino acid residue in the carboxypeptidase the activated form will be the native form of the carboxypeptidase.

If the Kex2 site is not attached directly to the natural N-terminal amino acid the liberated carboxypeptidase will contain an N-terminal extension of variable length or will lack one or more of the natural amino acid residues in the N-terminal end dependent of the position of the Kex2 site.

The activated carboxypeptidase can be used to process fusion proteins of any kind.

The caboxypeptidase may be expressed from any suitable promoter including its own promoter. However, it has turned out that the caboxypeptidase levels may be too high leading to aberrant processing of the insulin precursor. In order to find a suitable ratio between insulin precursor and active caboxypeptidase, the expression level of the caboxypeptidase mutant may be modulated by replacement of the caboxypeptidase's own promoter with alternative promoters.

If the caboxypeptidase is the CPY enzyme then suitable alternative promoters are promoter regions from the genes of CYC1, KEX2, MF(alpha)1 and MPD1, Alternatively, the amount of the proform of the carboxypeptidase may be regulated by modulating its expression from its promoter by changing the amount of transcription factors for the promoter in question.

In one embodiment of the invention the promoter for the carboxypeptidase is the Kex2 promoter.

Co-expression of the modified proform of the carboxypeptidase and an human insulin precursor in a fungi cell will enable secretion fully processed human insulin to the fermentation broth without the necessity of further expensive down stream processing steps. The expressed human insulin precursor will as the first step be intracellularly processed by the Golgi proteases Kex1 p and Kex2p. The human insulin precursor comprises a C-peptide which has been modified by the addition of extra amino acid residues (X) to the C-terminal amino acid residue in the B-chain of insulin. These extra amino acid residues are designed to facilitate an efficient cleavage of the C-peptide from the A and B chain of the insulin molecule within the fungi cell. Complete processing by Kex1 p and Kex2p results in a two-chain human insulin precursor molecule with the extension X of the C-terminal end of the B-chain. The precursors will have the form B—$(X)_n$...A, where B is the B-chain of human insulin, A is the A-chain of human insulin and X are the extra amino acid residues and where the A- and the B-chains are linked by two disulphide bridges as in human insulin.

This C-terminally extended, two chain human insulin will then be converted into mature human insulin or an analogue thereof by cleavage by the co-expressed and activated carboxypeptidase which will cleave off the B-chain C-terminal extension to give two chain mature human insulin or an analogue thereof as the case may be.

Depending on the amino acid residue in position B30 the carboxypeptidase may also take off the B30 amino acid residue resulting in a desB30 human insulin analogue. The carboxypeptidase may furthermore take of up to 5 amino acid residues from the C-terminal end of the B-chain resulting in a desB(29-30)-, desB 28-30)-, desB(27-30)- or desB(26-30) human insulin analogue.

Figure 5:
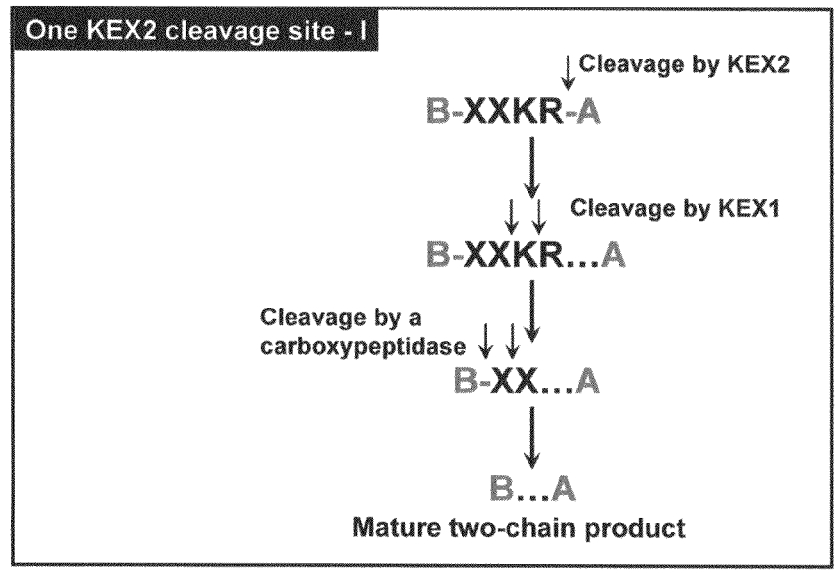
FIG. 5 shows a schematic review of the cleavage of an insulin precursor with one Kex2 site.
Figure 6:
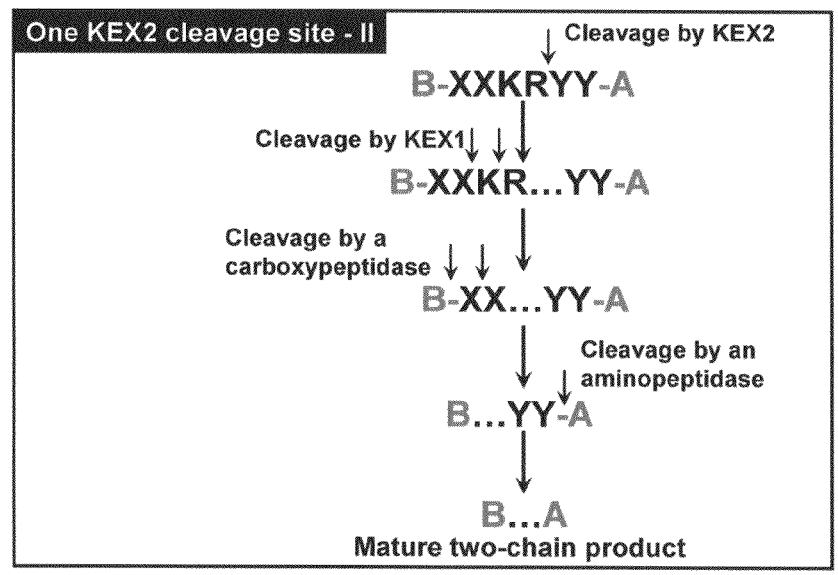
FIG. 6 shows the cleavage of an insulin precursor with one Kex2 site and an aminopeptidase site and
FIG. 7 shows the cleavage of an insulin precursor with two Kex2 sites
Figure 7:
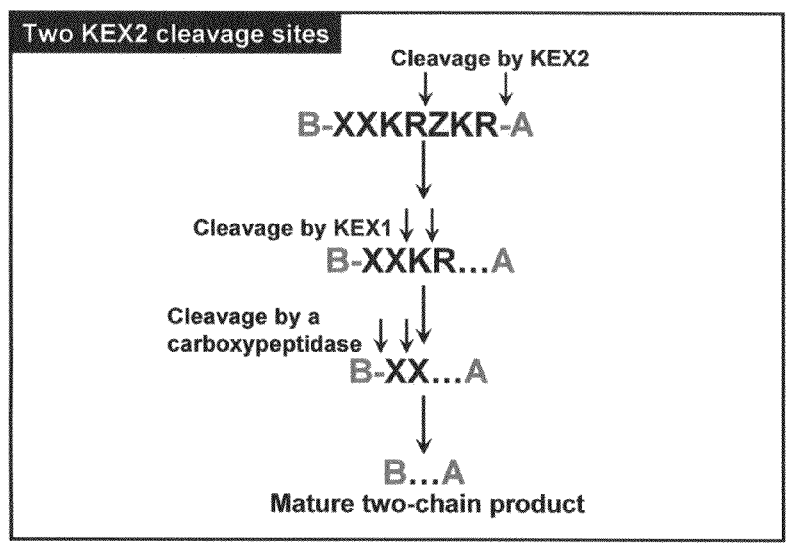

The various processing patterns of the insulin precursor are illustrated schematically in FIG. 5-7.

In FIG. 5 the insulin precursor construct has a single Kex2 site, KR, and a C-terminal extension of the B-chain illustrated by the sequence XX in the connecting peptide. The first processing step is cleavage at the Kex2 site by Kex2 which converts the single-chain structure to a two-chain structure having the sequence XXKR attached to the B-chain. Subsequently, the enzyme Kex1 will cleave off the KR-sequence and finally the carboxypeptidase cleaves off the XX-extension of the B-chain to give a mature two-chain insulin product.

In FIG. 6 an alternative embodiment is illustrated, where the insulin precursor has a single Kex2 site and an aminopeptidase cleavage site, YY, in the connecting peptide. As in FIG. 5, Kex2p, Kex1 p and the carboxypeptidase will remove the XX—KR sequence. However, in this embodiment a final aminopeptidase cleavage removes the YY-sequence to give the mature, two-chain insulin product.

In the embodiment illustrated in FIG. 7 the insulin precursor has two Kex2 cleavage sites connected by a peptide chain Z. The first cleavage with Kex2 removes the Z—KR sequence, the Kex1 removes the KR-sequence and finally carboxypeptidase removes the XX-sequence.

The production of high amounts of mature human insulin or insulin analogue from the fungi cell will significantly reduce the number of downstream purification steps necessary to produce an insulin product of a purity sufficiently high for pharmaceutical purposes. Thus, in the method for making insulin in yeast disclosed in U.S. Pat. No. 4,916,212 an insulin precursor is converted into human insulin in two steps i.e. a transpeptidation to convert the single chain insulin precursor B(1-29)-Alal-Ala-Lys-A(1-21) into an ester of human insulin and then a hydrolysis of the insulin ester into human insulin. Each conversion step will require an initial separation step and at least one subsequent purification step. Thus at least six additional steps are necessary to produce the mature insulin including at least one enzymatic conversion.

European patent application, 0163529A, PCT patent applications Nos. WO 95/02059 and WO 90/10075 disclose processes for making insulin and insulin analogues based on expression of a precursor of the insulin or insulin analogue in yeast that following initial recovery from the fermentation broth are enzymatically converted to the mature insulin or insulin analogue. The precursor molecules comprise certain modified C-peptides and may furthermore comprise an N-terminal extension of the insulin B-chain. The modified C-peptide and the possible N-terminal extension of the B-peptide are designed not to be cleaved in the yeast cell and thus the precursors are secreted as single chain peptides wherein the A- and the B-chain are still connected by the modified C-peptide but with correctly positioned disulphide bridges. The mature insulin or insulin analogue product is then obtained by a number of subsequent in vitro enzymatic steps to cleave the C-peptide and possibly the N-terminal extension. These enzymatic steps are time consuming, often costly and introduce additional impurities that subsequently have to be removed in further downstream process steps like expensive chromatography steps and the like.

It is well known that no enzymatic cleavage runs to a 100% cleavage leaving impurities of uncleaved or partially cleaved impurities which have to be efficiently removed in the case of pharmaceutical products. Thus, each cleavage step will be followed by at least one isolation or purification step, typically a chromatographic purification by means of exchange chromatography, gel filtration chromatography, affinity chromatography, or the like.

Chromatographic column material for use in commercial scale is very expensive and therefore reduction of the number of such chromatographic steps has a significant impact on the production economy. A reduction of the downstream conversion and purification step will in addition reduced the amount of labor work and hours spent in the process and thus further improve the production economy.

In the present process where the mature insulin or an analogue thereof can be isolated directly from the culture broth much fewer down stream process steps are necessary to produce a product of sufficient purity for pharmaceutical use.

The insulin molecule may be modified in the A- and/or B-chain as long as such modification do not have an adverse effect on the insulin activity of the resulting insulin analogue.

Thus, by "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues.

The insulin analogues will typically not comprise more than about 7 mutations, more typically not more than 5 and even more typically at the most 3 mutations compared to human insulin.

Over the years a fairly large number of modification of the insulin A- and or B-chain have been disclosed. Thus the position 28 of the B chain may be modified from the natural Pro residue to Asp, Lys, or Ile and Lys in position B29 may also be modified to Pro.

Also, Asn at position A21 may be modified to Ala, Gln, Glu, Gly, His, Ile, Leu, Met, Ser, Thr, Trp, Tyr or Val, in particular to Gly, Ala, Ser, or Thr and in particular to Gly.

Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Also, the natural amino acid residue in position A18 may be changed to a Gln residue or one or more of the amino acid residue in positions B26-B30 have been deleted.

Examples of insulin analogues which can be produced by the present method are $Gly^{A21}$ human insulin, $Gly^{A21}$ des(B30) human insulin, desB1 human insulin, des B30 human insulin, AspB28 human insulin and $Lys^{B28}Pro^{B29}$ human insulin.

Further examples of insulin analogues are human insulin analogues containing mutations in one or more of positions A21, B10, A8, A14, B25, B27 and B1.

The fungi cell may by any fungi cell as all fungi have the necessary proteolytic activity to cleave insulin precursor molecules of the present type to cleave off the connecting peptide and liberate a two chain molecule. However, over the years yeast has proven to be an efficient cell type for expressing and secreting of small peptides of the size of insulin. In particular the yeast *Saccharomyces cerevisiae* has proven to be useful.

Thus in one embodiment of the invention the fungi cell is a yeast cell and in a further embodiment the yeast cell is *Saccharomyces cerevisiae*.

The DNA sequence used in the present invention may be of genomic or cDNA origin, for instance be obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the insulin precursor may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the insulin precursor is operably linked to additional segments required for transcription of the DNA, such as a promoter. The promoter may be any DNA sequence which shows transcriptional activity in the host cell of choice and may be derived from genes encoding proteins either homologous or heterologous to the host cell.

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

The DNA sequence encoding the desired product may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

To direct the insulin into the secretory pathway of the host cells, a secretory signal sequence (also known as a leader sequence, prepro sequence or pre sequence) may be provided in the recombinant vector. The secretory signal sequence is joined to the DNA sequence encoding the insulin precursor in the correct reading frame. Secretory signal sequences are commonly positioned 5' to the DNA sequence encoding the peptide. The signal peptide may be a naturally occurring signal peptide, or a functional part thereof, or it may be a synthetic peptide.

For efficient secretion in yeast, a sequence encoding a leader peptide may also be inserted downstream of the signal sequence and upstream of the DNA sequence encoding the desired product.

Methods for transforming yeast cells with heterologous DNA and producing heterologous poly-peptides there from are described, e.g. in U.S. Pat. No. 4,599,311, U.S. Pat. No. 4,931,373, U.S. Pat. Nos. 4,870,008, 5,037,743, and U.S. Pat. No. 4,845,075. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373.

The medium used to culture the cells in the fermentation process may be any conventional medium suitable for growing the host cells, such as minimal or complex media containing appropriate supplements. Suitable media are available from commercial suppliers or may be prepared according to published recipes (e.g. in catalogues of the American Type Culture Collection). Thus the medium will contain at least one carbon source, one or several nitrogen sources, essential salts including salts of potassium, sodium, magnesium, phosphate, nitrate and sulphate, trace metals, water soluble vitamins, process aids including but not limited to protease inhibitors, stabilizers, ligands, antifoam agents and inducers. The medium may contain components which are partly precipitated or dispersed in the liquid medium at some operating conditions including sterilisation by heat. The medium can be made up by the mixing of several liquids and gaseous solutions. These solutions can be mixed prior to entering the fermentation tank or they are supplied to the fermentation tank as separate liquid streams added in a predefined ratio. The ratio between different liquid solutions of medium components can vary during the different stages of the fermentation process meaning that the overall composition of the medium may vary during the course of the fermentation.

The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

After isolation from the culture broth the mature insulin or insulin analogue may be converted into e.g. acylated forms by acylation of in particular the E-amino group of the B29Lys residue. Methods for acylation of insulins are well known in the art and disclosed in e.g. EP patents 792,290 and 894,095 and in U.S. Pat. Nos. 5,693,609, 5,646,242, 5,922,675, 5,750, 497 and 6,011,007.

Example of acylated insulins are $N^{\epsilon B29}$-tetradecanoyl des (B30) human insulin, $N^{\epsilon B29}$-lithocholoyl-γ-glutamyl des (B30) human insulin, $N^{\epsilon B29}$-($N^{\alpha}$-(HOOC(CH$_2$)$_{14}$CO)-γ-Glu) des(B30) human insulin or $N^{\epsilon B29}$-($N^{\alpha}$-(HOOC(CH$_2$)$_{16}$CO)-γ-Glu) des(B30) human insulin.

With "desB30" or "B(1-29)" is meant a natural insulin B chain or an analogue thereof lacking the B30 amino acid residue.

B(1-30) means the natural B chain of human insulin and "A(1-21)" means the natural insulin A chain. A18Q human insulin is an insulin analogue having a Gln in position A18 of the human insulin A-chain. B10E, A8H, A14E is an insulin analogue having a Glu in position B10, a His in position A8 and a Glu in position A14, respectively.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. Phe$^{B1}$ which means that the amino acid residue in position B1 is a phenylalanine residue.

With "C-peptide" is meant the peptide sequence linking the A- and B-peptide chains of the insulin molecule together.

With "mature insulin" is meant a two-chain insulin with the correct amino acid residue composition and the same structural conformation as the natural human insulin molecule i.e. with disulfide bridges between Cys$^{A7}$ and Cys$^{B7}$ and between Cys$^{A20}$ and Cys$^{B19}$ and an internal disulfide bridge between Cys$^{A6}$ and Cys$^{A11}$ and with insulin activity. Thus, a mature insulin according to the present invention would be human insulin. An analogue of mature human insulin may be B28Asp human insulin, desB30 human insulin, A14Glu, B25His human insulin and B31Leu, B32Ala human insulin.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by acylating a free amino group or a hydroxy group.

With "Kex2" or "Kex2p" is meant a subtilisin-like endoprotease that preferentially catalyzes cleavage after a sequence of two basic residues (lysine or arginine) (Rockwell, N.C., Krysan, D J, Komiyama, T & Fuller, R S 2002 Precursor Processing by Kex2/Furin Proteases. Chem. Rev. 102: 4525-4548).

With "Kex1" or "Kex1p" is meant a serine carboxypeptidase that preferentially catalyzes removal of C-terminal lysyl and/or arginyl residues (Shilton B H, Thomas D Y, Cygler M 1997 Crystal structure of Kex1deltap, a prohormone-processing carboxypeptidase from *Saccharomyces cerevisiae*. Biochemistry 36: 9002-9012).

With CPY is meant carboxypeptidase Y a carboxypeptidase that preferentially catalyses removal of hydrophobic or bulky C-terminal amino acid residues such as Phe and Leu (Remington, S. J. & Breddam, K. (1994) Carboxypeptidases C and D. *Methods Enzymol.* 244, 231-248). The amino acid sequence of CPY is disclosed by "Valls et al., 1987, Cell, 48(5):887-897.

With "correctly processed" is meant an enzymatic cleavage at the desired cleavage point giving the desired product with correct amino acid residue sequence.

"Efficient cleavage" is intended to mean a cleavage of at least 80%, preferably at least 85% and more preferably at least 95%.

"POT" is the *Schizosaccharomyces pombe* triose phosphate isomerase gene, and "TPI1" is the *S. cerevisiae* triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the host organism producing the protein.

Useful signal peptides for yeast host cells are obtained from the genes for *Saccharomyces cerevisiae* α-factor and *Saccharomyces cerevisiae* invertase. A number of signal peptides which may be used with the DNA construct of the invention including yeast aspartic protease 3 (Yps1) signal peptide or any functional analogue (Egel-Mitani et al. (1990) YEAST 6:127-137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143-180, Cold Spring Harbor Laboratory, NY and U.S. Pat. No. 4,870,008, the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897) and the yeast BAR1 signal peptide (cf. WO 87/02670).

The invention encompasses a vector which is capable of replicating in the selected microorganism or host cell and which carries a polynucleotide sequence encoding the insulin precursors of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In one embodiment, the recombinant expression vector is capable of replicating in yeast. Examples of sequences which enable the vector to replicate in yeast are the yeast plasmid 2 μm replication genes REP 1-3 and origin of replication.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125-130).

In a yeast host, useful promoters are the *Saccharomyces cerevisiae* MFα1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434).

The procedures used to ligate the DNA sequences coding for the insulin precursor, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, New York, 1989).

It will be understood that the vector may be constructed either by first preparing a DNA construct containing the entire DNA sequence encoding the insulin precursors of the invention, and subsequently inserting this fragment into a suitable expression vector, or by sequentially inserting DNA fragments containing genetic information for the individual elements followed by ligation.

The host cell used in the present invention is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In one embodiment the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces* and *Saccharomyces*). The basidiosporogenous yeasts include the genera *Leucosporidim, Rhodosporidium, Sporidiobolus, Filobasidium,* and *Filobasidiella.* Yeast belonging to the Fungi Imperfecti are divided into two families, Sporobolomycetaceae (e.g., genera *Sorobolomyces* and *Bullera*) and Cryptococcaceae (e.g., genus *Candida*). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomyces*, Strathern et al., editors, 1981).

The yeast host cell may be selected from a cell of a species of *Candida, Kluyveromyces, Saccharomyces, Schizosaccharomyces, Pichia, Hansenula, Yarrowia*. In one embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Sacchoromyces uvarum, Pichia kluyveri, Yarrowia lipolytica, Candida utilis, Candida cacaoi,* and *Geotrichum fermentans.* Other useful yeast host cells are a *Kluyveromyces lactis, Kluyveromyces fragilis, Hansenula polymorpha, Pichia pastoris Yarrowia lipolytica, Schizosaccharomyces pombe, Ustilgo maylis, Candida maltose, Pichia guillermondii* and *Pichia methanoliol* (cf. Gleeson et al., *J. Gen. Microbiol.* 132, 1986, pp. 3459-3465; U.S. Pat. No. 4,882,279 and U.S. Pat. No. 4,879,231).

The expression "a codable amino acid" or "a codable amino acid residue" is used to indicate an amino acid or amino acid residue which can be coded for by a triplet ("codon") of nucleotides.

In the present context the three-letter or one-letter indications of the amino acids have been used in their conventional meaning. Unless indicated explicitly, the amino acids mentioned herein are L-amino acids. Further, the left and right ends of an amino acid sequence of a peptide are, respectively, the N- and C-termini unless otherwise specified.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

General Procedures

All expressions plasmids are of the C-POT type, similar to those described in EP 171, 142. These are 2µ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator (FIG. 1). These sequences are similar to the corresponding sequences in plasmid pKFN1003 (described in WO 9010075) as are all sequences except the following: 1) the sequence of the EcoRI-XbaI fragment encoding the fusion protein of the leader and the insulin product and 2) a silent mutation has been introduced resulting in removal of a NcoI-site in the 2µ-region in the expression vector. In order to facilitate cloning of different fusion proteins the DNA sequence encoding the MFα1 pre-pro leader has been changed to incorporate a NcoI site (see FIG. 2) and is called the MFα1* pre-pro leader. Thus the NcoI-XbaI fragment is simply replaced by an NcoI-XbaI fragment encoding the insulin construct of interest. Such NcoI-XbaI fragments may be synthesized using synthetic oligonucleotides and PCR according to standard techniques. In addition to the alpha-leader other leaders can be used.

Yeast transformants were prepared by transformation of the host strains *S. cerevisiae* strain MT663 or ME1719. The yeast strain MT663 (MATa/MATα pep4-3/pep4-3 HIS4/his4 Δtpi::LEU2/Δtpi::LEU2 Cir') was deposited in the Deutsche Sammlung von Mikroorganismen und Zellkulturen in connection with filing WO 92111378 and was given the deposit number DSM 6278. *S. cerevisiae* strain ME1719 (MATa/α leu2/leu2 pep4-3/pep4-3 Δtpi::LEU2/Δtpi::LEU2 Δura3/Δura3 Δyps1::URA3/Δyps1::ura3 Cir+) is described in WO 98/01535.

MT663 or ME1719 were grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM $Na_2$EDTA pH=8.0 and 6.7 mglml dithiothreitol. The suspension was incubated at 30° C. for 15 minutes, centrifuged and the cells resuspended in 10 ml of a solution containing 1.2 M sorbitol, 10 mM Na2EDTA. 0.1 M sodium citrate, pH 0 5.8, and 2 mg NovozymC3234. The suspension was incubated at 30° C. for 30 minutes, the cells collected by centrifugation, washed in 10 ml of 1.2 M sorbitol and 10 ml of CAS (1.2 M sorbitol, 10 mM $CaCl_2$, 10 mM Tris HCl (Tris=Tris(hydroxymethy1)-aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM $CaCl_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium.

Example 1

Construction of a yeast expression system for the human insulin precursor B(1-30)-LARRDLGKR(SEQ ID NO:9)-(A1-21), (A14E, B25H) human insulin.

FIG. 1 shows a yeast plasmid called pESI42-33. The plasmid contains an expression cassette comprising an EcoRI-XbaI fragment inserted into the plasmid between the transcription-promoter and the transcription-terminator of the S. cerevisiae TPI gene. In plasmid pESI42-33 the EcoRI-XbaI fragment encodes a fusion product composed of the MFα1* pre-pro leader, a Lys-Arg cleavage site for the dibasic processing endopeptidase Kex2, and the insulin precursor B(1-30)-LARRDLGKR(SEQ ID NO:9)-(A1-21), (A14E, B25H) human insulin.

A DNA fragment containing sequences encoding the insulin precursor B(1-30)-LARRDLGKR(SEQ ID NO:9)-(A1-21), (A14E, B25H) human insulin was constructed using synthetic oligonucleotides and standard PCR amplifications. The resulting PCR fragment was purified, digested with NcoI and XbaI and ligated to the NcoI-XbaI vector fragment of the modified cPOT type expression vector (FIG. 1)

The expression plasmid was propagated in E. coil, grown in the presence of ampicillin and isolated using standard techniques (Sambrook et al., 1989). The plasmid DNA was checked for insert by appropriate restriction nucleases (e.g. EcoRI, NcoI, XbaI) and was shown by sequence analysis to contain the proper sequence of the human insulin precursor B(1-30)-LARRDLGKR(SEQ ID NO:9)-(A1-21), (A14E, B25H) human insulin.

The plasmid was transformed into S. cerevisiae strain MT663. Yeast transformants harbouring the plasmid were selected by glucose utilization as carbon source on YPD (1% yeast extract, 2% peptone, 2% glucose) agar (2%) plates.

Example 2

Construction of a yeast expression system for the CPY activation mutants.

Figure 2:
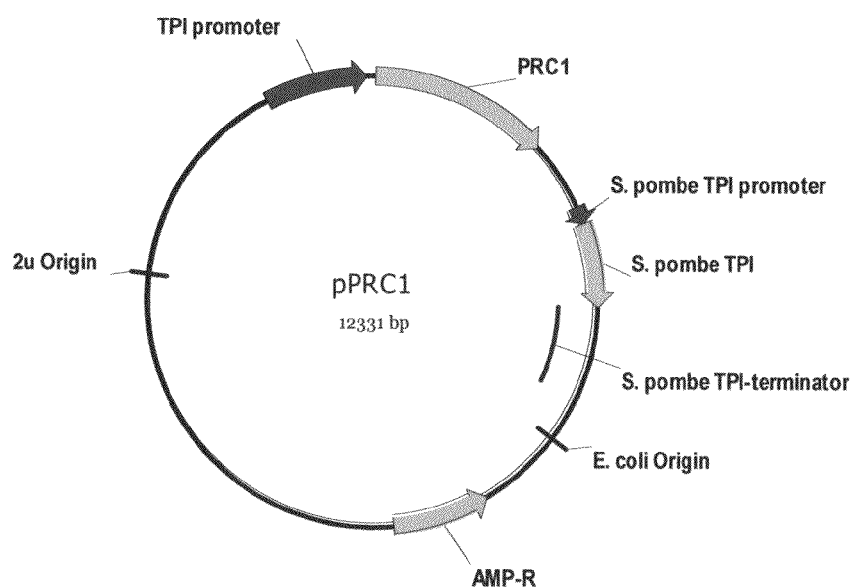
FIG. 2 shows plasmid pRC1.

FIG. 2 shows a yeast plasmid called pPRC1. The plasmid contains an expression cassette comprising an ClaI-NheI fragment inserted into the plasmid between the transcription-promoter and the transcription-terminator of the S. cerevisiae TPI gene. In plasmid pPRC1 the ClaI-NheI fragment encodes wildtype pre-pro-CPY. All CPY mutant plasmids are identical to pPRC1 except for the relevant point mutations made for introduction of dibasic Kex2 cleavage motifs.

The DNA fragments containing sequences encoding PRC1 mutated for insertion of Kex2 cleavage sites were constructed using synthetic oligonucleotides, genomic yeast DNA as template and standard PCR amplifications. The resulting PCR fragments were purified, digested with ClaI and NheI and ligated to the ClaI-NheI vector fragment of the modified cPOT type expression vector.

The expression plasmid was propagated in E. coil, grown in the presence of ampicillin and isolated using standard techniques (Sambrook et al., 1989). The plasmid DNA was checked for insert by appropriate restriction nucleases and was shown by sequence analysis to contain the proper sequence of the PRC1

The plasmid was transformed into S. cerevisiae strain MT663. Yeast transformants harbouring the plasmid were selected by glucose utilization as carbon source on YPD (1% yeast extract, 2% peptone, 2% glucose) agar (2%) plates.

Example 3

Construction of a yeast system for co-expression of the insulin precursor B(1-30)-LARRDLGKR(SEQ ID NO:9)-(A1-21), (A14E, B25H) human insulin and a CPY activation mutants.

Figure 3:
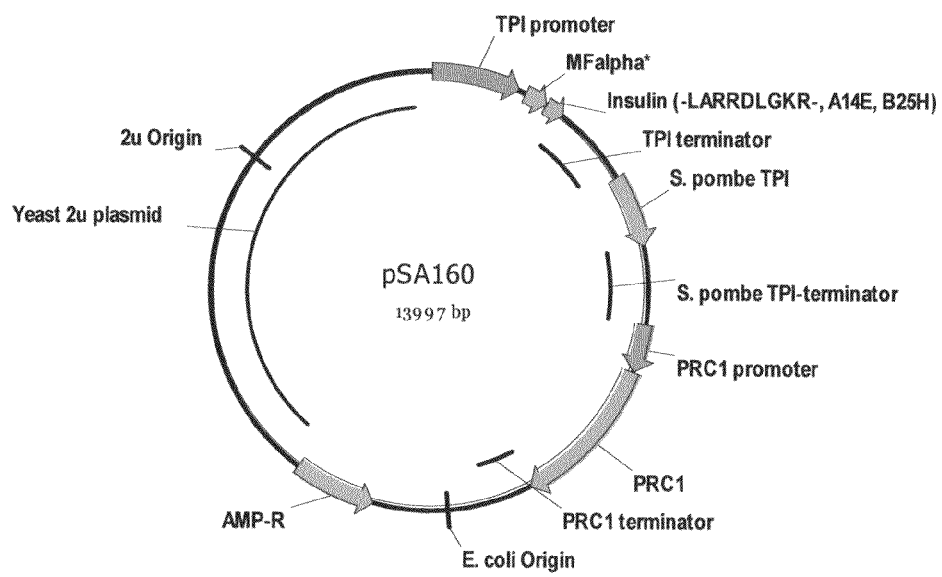
FIG. 3 shows plasmid pSA160.

FIG. 3 shows a yeast plasmid called pSA160. The plasmid contains an expression cassette comprising an EcoRI-XbaI fragment inserted into the plasmid between the transcription-promoter and the transcription-terminator of the S. cerevisiae TPI gene. In plasmid pSA160, the EcoRI-XbaI fragment encodes a fusion product composed of the MFα1* pre-pro leader, a Lys-Arg cleavage site for the dibasic processing endopeptidase Kex2, and the insulin precursor B(1-30)-LARRDLGKR(SEQ ID NO:9)-(A1-21), (A14E, B25H) human insulin. The plasmid also contains an expression cassette encoding the CPY mutant "F" comprising a KpnI-SacI fragment inserted into the plasmid between after the transcription-promoter of the S. cerevisiae PRC1 gene.

The insulin cassette was subcloned into a suitable cPOT type expression vector. Subsequently, the PRC1 promoter was amplified by PCR using genomic yeast DNA as template and cloned into the above plasmid as a SalI-KpnI fragment. Finally, the DNA encoding the CPY mutant plus terminator was amplified using PCR and cloned into the plasmid.

The expression plasmid was propagated in E. coli, grown in the presence of ampicillin and isolated using standard techniques (Sambrook et al., 1989). The plasmid DNA was checked for insert by appropriate restriction nucleases and was shown by sequence analysis to contain the proper sequence of the PRC1 open reading frame.

The plasmid was transformed into S. cerevisiae strain MT663. Yeast transformants harbouring the plasmid were selected by glucose utilization as carbon source on YPD (1% yeast extract, 2% peptone, 2% glucose) agar (2%) plates.

Example 4

A number of CPY mutants were constructed. The plasmids were transformed into yeast, and lab scale batch fermentations were performed by cultivation in a defined media for 72 hours at 30° C. The fermentation broth was assayed for CPY activity using the synthetic substrate N-(3-[2-Furyl]acryloyl)-Phe-Phe. Using this substrate, CPY activity can be followed spectrophotometrically as a change in absorbance at 337 nm. By correlating the activity to the activity of a CPY standard with known concentration, the concentration in the supernatant can be estimated. Based on these assays, the 9 mutants were estimated to be present in a concentration of 0-2.3 mg/L.

| Mutant | Concentration of active CPY (mg/L) |
|---|---|
| A | 0.21 |
| B | 0.41 |
| C | 0.30 |
| D | 0.13 |
| E | 0.85 |
| F | 2.25 |
| G | 0.02 |

In order to examine the degree of processing, the fermentation supernatants were subjected to western blot analysis, probing with CPY antibodies. The ratio between unprocessed CPY (proCPY) and processed CPY was estimated from the blot. This showed up to ~80% conversion to mature CPY in the best of the mutants.

Example 5

Figure 4:
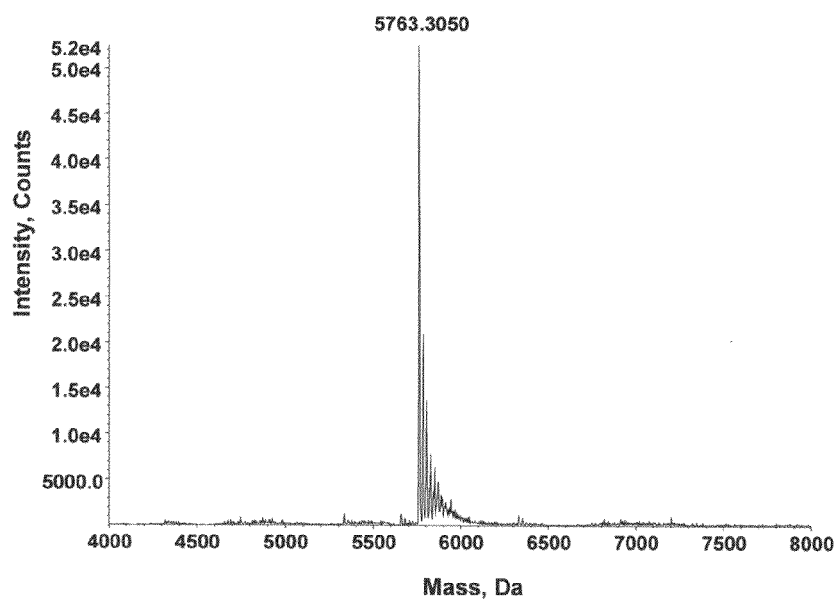
FIG. 4 shows a deconvoluted mass spectrum of a 24 hours culture supernatant of a strain harbouring pSA160. The mass 5763 corresponds to fully processed A14E, B25H insulin

The plasmid pSA160 for co-expression of the human insulin precursor (B(1-30)-LARRDLGKR(SEQ ID NO:9)-(A1-21), (A14E, B25H) human insulin and the CPY activation mutant "F" was transformed into yeast and lab scale batch fermentations were performed by cultivation in a defined media at 30° C. The fermentation broth was analysed by LC-MS after 24 hours cultivation insulin species. This showed that >90% of the secreted insulin species were fully processed A14E, B25H human insulin analogue. FIG. 4 demonstrates the successful removal of the LA-extension from the C-terminal of the insulin B-chain by the secreted active CPY.

Example 6

Continuous fermentation of a yeast strain harbouring the co-expression plasmid described in Example 3 showed that CPY levels were too high, leading to aberrant processing of the human insulin precursor. In order to find a suitable ratio between the human insulin precursor and active CPY, the expression level of the CPY mutant was modulated by replacement of the PRC1 promoter with alternative promoters.

The promoter regions from the genes of CYC1, KEX2, MF(alpha)1, and MPD1, were amplified by PCR and cloned into the SalI-KpnI sites of the co-expression plasmid described in Example 3 resulting in an exchange of the PRC1 promoter sequence for the alternative CYC1, KEX2, MF(alpha)1, and MPD1 promoter sequences, respectively. The resulting plasmids were transformed into S. cerevisiae strain MT663. Yeast transformants harbouring the plasmid were selected by glucose utilization as carbon source on YPD (1% yeast extract, 2% peptone, 2% glucose) agar (2%) plates.

Example 7

Lab scale batch fermentations were performed with the new yeast strains harbouring the plasmids described in Example 6. The strains were cultivated in defined media at 30° C. After 72 hours, the concentration of active CPY in the fermentation broth was determined by measuring the activity using a chromogenic substrate, FA-Phe-Phe. The results show a broad range of expression levels.

| Promoter | CPY concentration relative to the PRC1 promoter (%) |
|---|---|
| CYC1 | 0.3 |
| KEX2 | 0.9 |
| MF(alpha)1 | 0.07 |
| MPD1 | 4.3 |
| PRC1 | 100 |

Example 8

Continuous fermentations were performed with the yeast strains harbouring the co-expression plasmids for co-expression of the human insulin precursor B(1-30)-LARRDLGKR (SEQ ID NO:9)-(A1-21), (A14E, B25H) human insulin and a CPY activation mutants described in Example 6. The KEX2 promoter gave expression levels of CPY that resulted in a very low percentage of aberrant processed A14, B25 human insulin.

| Promoter | % correctly processed insulin |
|---|---|
| PRC1 | 80 |
| KEX2 | 95 |

The invention claimed is:

1. A method for making an activated carboxypeptidase in a fungi cell, wherein the fungi cell has a non-functional PEP4 gene, and wherein a DNA sequence encoding a modified proform of the carboxypeptidase comprising an inserted Kex2 cleavage site is expressed under conditions suitable for expression of the modified proform of the carboxypeptidase whereupon the prosequence is cleaved off within the cell to liberate the free, active form of the carboxypeptidase.

2. The method according to claim 1 further comprising a step of isolating the active form of the carboxypeptidase from the fungi cell.

3. The method according to claim 1, wherein the carboxypeptidase is endogenous to the host fungi cell.

4. The method according to claim 1, wherein the Kex2 site has been inserted in the proform of the carboxypeptidase in a position from 0 to about 30 amino acid residues upstream or downstream to the natural N-terminal amino acid residue in the wildtype carboxypeptidase.

5. The method according to claim 4, wherein the Kex2 cleavage site is inserted in the prosequence in a distance of from 5-20, 5-15 or 5-10 amino acid residues upstream to the natural N-terminal amino acid residue in the wildtype form of the carboxypeptidase.

6. The method according to claim 5, wherein the Kex2 cleavage site is inserted in a position from 2-20, 2-15 or 2-10 amino acid residues upstream to the N-terminal amino acid residue of the wildtype carboxypeptidase enzyme.

7. The method according to claim 1, wherein the carboxypeptidase is CPY.

8. A method for making mature human insulin or an analogue thereof by reacting a precursor of human insulin or an analogue thereof comprising a C-terminal extension of the B-chain with a carboxypeptidase produced by a method according to claim 1 whereby the C-terminal extension of the B-chain is cleaved off to give mature human insulin or an analogue thereof.

* * * * *